United States Patent
Augier et al.

(10) Patent No.: US 12,312,288 B2
(45) Date of Patent: May 27, 2025

(54) GAS/LIQUID OLIGOMERIZATION REACTOR COMPRISING TRANSVERSE INTERNALS

(71) Applicant: IFP Energies nouvelles, Rueil-Malmaison (FR)

(72) Inventors: Frederic Augier, Rueil-Malmaison (FR); Alexandre Vonner, Rueil-Malmaison (FR); Pedro Maximiano Raimundo, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 17/785,525

(22) PCT Filed: Dec. 8, 2020

(86) PCT No.: PCT/EP2020/085018
§ 371 (c)(1),
(2) Date: Jun. 15, 2022

(87) PCT Pub. No.: WO2021/122139
PCT Pub. Date: Jun. 24, 2021

(65) Prior Publication Data
US 2023/0042372 A1 Feb. 9, 2023

(30) Foreign Application Priority Data
Dec. 18, 2019 (FR) ...................... 1914760

(51) Int. Cl.
*C07C 2/08* (2006.01)
*B01J 19/00* (2006.01)
(Continued)

(52) U.S. Cl.
CPC ............... *C07C 2/08* (2013.01); *B01J 19/006* (2013.01); *B01J 19/24* (2013.01); *C07C 2/24* (2013.01);
(Continued)

(58) Field of Classification Search
None
See application file for complete search history.

(56) References Cited

U.S. PATENT DOCUMENTS 4,242,531 A 12/1980 Carter
4,456,504 A * 6/1984 Spars .................... B01J 8/12
201/31

(Continued)

FOREIGN PATENT DOCUMENTS

DE 4338414 C1 * 3/1995 ............... B01J 3/04
EP 1777208 B1 2/2010
(Continued)

OTHER PUBLICATIONS

International Search Report PCT/EP2020/085018 dated Feb. 16, 2021 (pp. 1-2).

*Primary Examiner* — Jennifer A Leung
(74) *Attorney, Agent, or Firm* — MILLEN, WHITE, ZELANO & BRANIGAN, P.C.; Ryan R. Pool

(57) ABSTRACT

The present invention relates to the field of gas/liquid reactors making possible the oligomerization of ethylene to give linear olefins by homogeneous catalysis with a reaction chamber comprising transverse internals capable of slowing down the ascent of the gaseous ethylene in the said reactor.

16 Claims, 6 Drawing Sheets

(51) Int. Cl.
   *B01J 19/24* (2006.01)
   *C07C 2/24* (2006.01)
(52) U.S. Cl.
   CPC ............... *B01J 2219/00166* (2013.01); *B01J 2219/00765* (2013.01)

(56) References Cited

U.S. PATENT DOCUMENTS

| | | | |
|---|---|---|---|
| 4,532,370 A | | 7/1985 | Le Quan et al. |
| 4,615,998 A | | 10/1986 | Le Quan et al. |
| 5,498,742 A | * | 3/1996 | Buysch ............... C07C 68/01 558/274 |
| 5,523,451 A | * | 6/1996 | Rechner ............... C07C 68/06 558/270 |
| 6,436,245 B1 | * | 8/2002 | Nishimura ........... B01D 3/225 203/99 |
| 9,598,329 B2 | | 3/2017 | Shaik et al. |
| 9,931,622 B2 | | 4/2018 | Magna et al. |
| 10,022,698 B2 | | 7/2018 | Shaik et al. |
| 10,150,108 B2 | | 12/2018 | Magna et al. |
| 10,646,860 B2 | | 5/2020 | Breuil et al. |
| 11,207,657 B2 | | 12/2021 | Augier et al. |
| 2009/0203947 A1 | | 8/2009 | Schneider et al. |
| 2013/0158321 A1 | | 6/2013 | Olivier-Bourbigou et al. |
| 2015/0273456 A1 | | 10/2015 | Magna et al. |
| 2016/0002124 A1 | | 1/2016 | Magna et al. |
| 2017/0081256 A1 | * | 3/2017 | Kreischer ............... B01J 19/18 |
| 2018/0318819 A1 | | 11/2018 | Breuil et al. |
| 2019/0001317 A1 | | 1/2019 | Breuil et al. |
| 2019/0126232 A1 | | 5/2019 | Girgis et al. |

FOREIGN PATENT DOCUMENTS

| | | | | |
|---|---|---|---|---|
| WO | WO-9939815 A1 | * | 8/1999 | ............ B01D 53/18 |
| WO | 2013170110 A1 | | 11/2013 | |

* cited by examiner

Prior Art

GAS/LIQUID OLIGOMERIZATION REACTOR COMPRISING TRANSVERSE INTERNALS

TECHNICAL FIELD

The present invention relates to the field of gas/liquid reactors making possible the oligomerization of ethylene to give linear olefins by homogeneous catalysis with a reaction chamber comprising transverse internals capable of slowing down the ascent of the gaseous ethylene in the said reactor.

The invention also relates to the use of the said gas/liquid reactor in a process for the oligomerization of ethylene to give linear α-olefins, such as but-1-ene, hex-1-ene or oct-1-ene, or a mixture of linear α-olefins.

PRIOR ART

The invention relates to the field of gas/liquid reactors, also known as a bubble column, and also to the uses thereof in an ethylene oligomerization process. One disadvantage encountered during the use of such reactors in ethylene oligomerization processes is the management of the gas headspace, corresponding to the upper part of the reactor in the gaseous state. The said gas headspace comprises gaseous compounds of low solubility in the liquid phase, compounds which are partially soluble in the liquid but which are inert, and also gaseous ethylene not dissolved in the said liquid. The passage of gaseous ethylene from the liquid lower part of the reaction chamber to the gas headspace is a phenomenon referred to as breakthrough. In point of fact, the gas headspace is bled in order to remove the said gaseous compounds. When the amount of gaseous ethylene present in the gas headspace is high, the bleeding of the gas headspace leads to a not insignificant loss of ethylene, which is detrimental to the productivity and to the cost of the oligomerization process. Furthermore, a significant breakthrough phenomenon means that a great deal of gaseous ethylene was not dissolved in the liquid phase and thus was not able to react, which is detrimental to the productivity and to the selectivity of the oligomerization process.

In order to improve the efficiency of the oligomerization process in terms of productivity and of cost, it is thus essential to limit the phenomenon of breakthrough of the ethylene in order to improve its conversion in the said process, while retaining a good selectivity for desired linear α-olefins.

The processes of the prior art employing a gas/liquid reactor, as illustrated in FIG. 1, do not make it possible to limit the loss of gaseous ethylene, and the bleeding of the gas headspace results in a departure of gaseous ethylene from the reactor which is harmful to the yield and the cost of the process.

The Applicant Company has described, in Applications WO2019/011806 and WO2019/011609, processes which make it possible to increase the contact surface area between the upper part of the liquid fraction and the gas headspace via dispersion or vortex means, in order to promote the passage of the ethylene contained in the gas headspace to the liquid phase at the liquid/gas interface. These processes do not make it possible to limit the phenomenon of breakthrough and are insufficient when the amount of ethylene in the gas headspace is substantial because of a high level of breakthrough.

Moreover, during these research studies, the Applicant Company has found that, in a reactor operating with a constant flow rate of injected gaseous ethylene, the amount of dissolved ethylene and thus the level of breakthrough are dependent on the dimensions of the reactors implementing the process and in particular on the height of the liquid phase. This is because the lower the height, the shorter the time during which the gaseous ethylene travels through the liquid phase to dissolve and the higher the level of breakthrough.

The Applicant Company has discovered that it is possible to improve the conversion of olefin(s), while retaining a high selectivity for desired linear olefin(s), and in particular for α-olefin(s), by limiting the phenomena of breakthrough by means of a gas/liquid reactor which makes it possible to increase the residence time of the gaseous ethylene in the liquid phase by means of internals capable of slowing down the ascent of the gaseous ethylene.

This is because a reactor according to the present invention makes it possible to slow down the ascent of the gaseous ethylene, which has the effect of improving the dissolution of the gaseous ethylene and thus of limiting the phenomenon of breakthrough for a given volume of liquid phase.

The invention also relates to a process for the oligomerization of olefins and in particular of ethylene employing the reactor according to the invention comprising at least two transverse internals.

SUBJECT-MATTER OF THE INVENTION

The Applicant Company has developed a gas/liquid reactor for the oligomerization of gaseous ethylene which can contain a liquid phase and a gas headspace, the said reactor comprising:
  a chamber 1 of elongated shape along the vertical axis,
  a means for introduction of gaseous ethylene 2, located in the lower part of the reaction chamber,
  a means for withdrawal 5 of a liquid reaction effluent, located in the lower part of the reaction chamber,
  a means for bleeding off 4 a gaseous fraction, located at the top of the said reactor,
in which:
  the said chamber 1 comprises at least two transverse internals 11 positioned over at least a part of a section of the chamber (1) of the said reactor so as to increase the residence time of the gaseous ethylene in the liquid phase,
  each of the said internals exhibiting at least one opening 12 with a hydraulic diameter between 21 and 500 mm, and
  the said opening 12 or the sum of the openings for an internal occupying between 20% and 80% of the total surface area of a cross section of the reaction chamber on which the said internal is located.

In a preferred embodiment, the transverse internals are arranged so as to increase the residence time of the gaseous ethylene, by disrupting the ascent of the gaseous ethylene within the liquid phase.

In a preferred embodiment, the transverse internals exhibit at least one opening 12 with a hydraulic diameter between 25 and 450 mm, preferably between 30 and 400 mm.

In a preferred embodiment, the transverse internals exhibit a plurality of openings with a hydraulic diameter between 21 and 500 mm, preferentially between 25 and 450 mm, preferably between 30 and 400 mm.

In a preferred embodiment, the said one opening or the sum of the openings occupy/occupies between 25% and 75% of the total surface area of a cross section of the chamber on which the said internal is located, preferably between 40% and 70%, preferably between 40% and 60% and in a preferred way between 45% and 55%.

In a preferred embodiment, the transverse internals extend radially over the entire section of the chamber 1 of the said reactor, so as to be able to slow down the ascent of the gaseous ethylene in the liquid phase.

In a preferred embodiment, the transverse internals are chosen from a perforated plate, a slit tray, such as a grid, tray having valves, discs and rings.

In a preferred embodiment, the transverse internals extend radially over a part of the section of the chamber 1 of the said reactor, so as to be able to slow down the ascent of the gaseous ethylene in the liquid phase.

In a preferred embodiment, the transverse internals are chosen from flat, curved or pyramidal lateral plates or any other internal capable of acting as baffle.

In a preferred embodiment, the said reactor comprises at least two transverse internals extending partially over a part of the section of the said chamber, the said internals being positioned alternately on the walls of the chamber 1.

In a preferred embodiment, the chamber comprises a number of transverse internals between 2 and 30, preferably between 2 and 20, preferably between 2 and 15.

In a preferred embodiment, the said reactor additionally comprises a means for withdrawal of a gaseous fraction at the gas headspace of the reaction chamber and a means for introduction of the said withdrawn gaseous fraction into the liquid phase in the lower part of the reaction chamber.

In a preferred embodiment, the said reactor additionally comprises a recirculation loop comprising a withdrawal means on the lower part of the reaction chamber, preferably at the bottom, so as to withdraw a liquid fraction to one or more heat exchanger(s) capable of cooling the said liquid fraction, and a means for introduction of the said cooled fraction into the upper part of the reaction chamber.

Another subject-matter of the present invention relates to a process for the oligomerization of gaseous ethylene employing the reactor according to any one of the preceding embodiments.

In a preferred embodiment, the oligomerization process is carried out at a pressure between 0.1 and 10.0 MPa and at a temperature between 30 and 200° C., comprising the following stages:
  a stage a) of introduction of a catalytic oligomerization system comprising a metal catalyst and an activating agent into a reaction chamber,
  a stage b) of bringing the said catalytic system into contact with gaseous ethylene by the introduction of the said gaseous ethylene into the lower zone of the reaction chamber,
  a stage c) of withdrawal of a liquid fraction,
  a stage d) of cooling the fraction withdrawn in stage c) by passing the said fraction through a heat exchanger,
  a stage e) of introduction of the fraction cooled in stage d) into the upper part of the lower zone of the reaction chamber,
  an optional stage of recycling a gaseous fraction, withdrawn at the gas headspace of the reaction chamber and introduced at the lower part of the reaction chamber, into the liquid phase.

Definitions & Abbreviations

The following terms are defined in order to improve the understanding of the invention:

The term "oligomerization" denotes any addition reaction of a first olefin with a second olefin identical to or different from the first olefin and comprises dimerization, trimerization and tetramerization. The olefin thus obtained is of $C_nH_{2n}$ type, where n is equal to or greater than 4.

The term "olefin" denotes both an olefin and a mixture of olefins.

The term "α-olefin" denotes an olefin in which the double bond is located at the terminal position of the alkyl chain.

The term "heteroatom" is an atom other than carbon and hydrogen. A heteroatom can be chosen from oxygen, sulfur, nitrogen, phosphorus, silicon and halides, such as fluorine, chlorine, bromine or iodine.

The term "hydrocarbon" is an organic compound consisting exclusively of carbon (C) and hydrogen (H) atoms of empirical formula $C_mH_p$, with m and p natural integers.

The term "catalytic system" denotes a mixture of at least one metal precursor, of at least one activating agent, optionally of at least one additive and optionally of at least one solvent.

The term "alkyl" is a saturated or unsaturated, linear or branched, non-cyclic, cyclic or polycyclic hydrocarbon chain comprising between 1 and 20 carbon atoms, preferably from 2 to 15 carbon atoms and more preferably still from 2 to 8 carbon atoms, denoted $C_1$-$C_{20}$ alkyl. For example, $C_1$-$C_6$ alkyl is understood to mean an alkyl chosen from the methyl, ethyl, propyl, butyl, pentyl, cyclopentyl, hexyl and cyclohexyl groups.

The term "aryl" is a fused or non-fused, mono- or polycyclic, aromatic group comprising between 6 and 30 carbon atoms, denoted $C_6$-$C_{30}$ aryl.

The term "alkoxy" is a monovalent radical consisting of an alkyl group bonded to an oxygen atom, such as the $C_4H_9O$— group.

The term "aryloxy" is a monovalent radical consisting of an aryl group bonded to an oxygen atom, such as the $C_6H_5O$— group.

The term "lower part" of the chamber of the gas/liquid reactor denotes the lower half of the reactor and of the reaction zone.

The term "upper part" of the reaction chamber of the gas/liquid reactor denotes the upper half of the reactor or of the reaction zone.

The term "withdrawal flow rate" denotes the weight of liquid withdrawn from the reactor per unit of time; it is expressed in tonnes per hour (t/h).

The term "non-condensable gas" denotes an entity in gaseous physical form which only partially dissolves in the liquid at the temperature and pressure conditions of the reaction chamber and which can, under certain conditions, accumulate in the headspace of the reactor (example here: ethane).

Liquid phase is understood to mean the mixture of all of the compounds which are in a liquid physical state under the temperature and pressure conditions of the reaction chamber, it being possible for the said phase to comprise gaseous compounds, such as gaseous ethylene, in the form of bubbles.

Gas headspace is understood to mean the upper part of the chamber in the gaseous state, located at the top of the reaction chamber, that is to say directly above the liquid phase and consisting of a mixture of compounds which are in the gaseous physical state during the use of a reactor in an oligomerization process.

Lateral lower part of the reaction chamber is understood to mean a part of the shell of the reaction chamber of the reactor located in the bottom part and on the side.

t/h is understood to mean the value of a flow rate expressed in tonnes per hour and kg/s is understood to mean the value of a flow rate in kilograms per second.

The terms reactor or device denote all of the means which make possible the implementation of the oligomerization process according to the invention, such as in particular the reaction chamber and the recirculation loop.

Bottom of the reaction chamber is understood to mean the lower quarter of the reaction chamber.

Top of the reaction chamber is understood to mean the upper quarter of the reaction chamber.

Transverse denotes the surface, the internal or also the section which are perpendicular to the vertical axis of the chamber.

The term "solvent" denotes a liquid which has the property of dissolving, diluting or extracting other substances without chemically modifying them and without itself being modified. The expression "between . . . and . . . " should be understood as including the limits mentioned.

The terms "chamber" or "reaction chamber" denote the wall of the reactor in which the oligomerization reaction takes place.

Degree of saturation is understood to mean the percentage of ethylene dissolved in the liquid phase with respect to the maximum amount of ethylene which might be dissolved in the said liquid phase, defined by the thermodynamic equilibrium between the partial pressure of gaseous ethylene and the said liquid phase. The degree of saturation can be measured by gas chromatography.

The hydraulic diameter (HD) is defined for an opening by the formula HD=4A/P, in which A denotes the area of the opening (expressed in $mm^2$) and P denotes the perimeter of the said opening (expressed in mm), i.e. four times the area of the opening divided by the perimeter of the said opening.

Upward flow denotes the direction of the gaseous ethylene travelling through the liquid phase within the reactor.

DETAILED DESCRIPTION OF THE INVENTION

Figure 1:
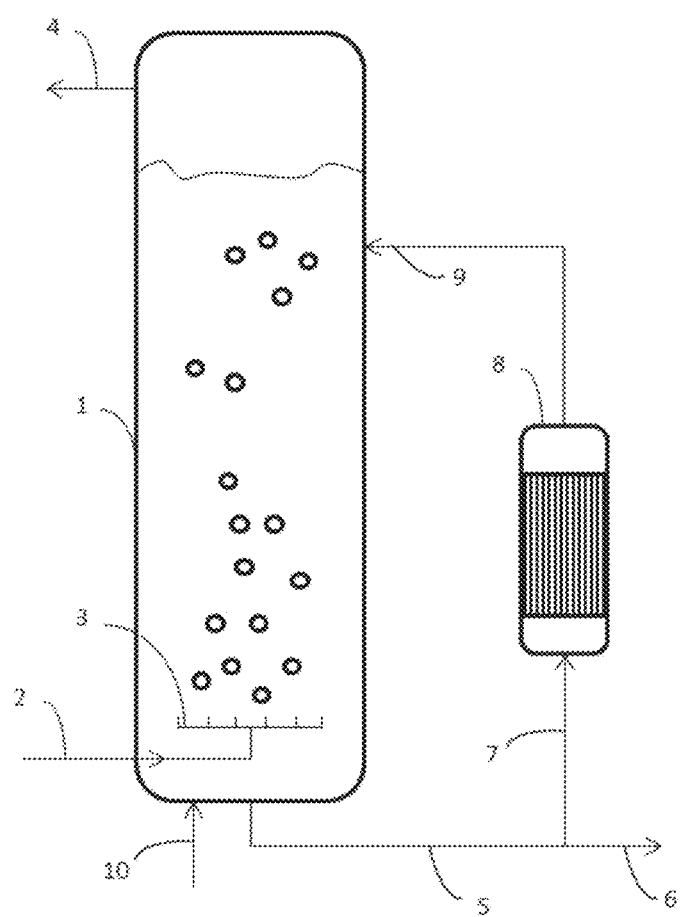
FIG. 1 illustrates a gas/liquid reactor according to the prior art. This device consists of a reaction chamber 1 comprising a lower part comprising a liquid phase, an upper part comprising a gas headspace, and a means for introduction of gaseous ethylene 2 into the liquid phase via a gas distributor 3. The upper part comprises a bleeding means 4. A pipe for the withdrawal of a liquid fraction 5 is located in the bottom of the reaction chamber 1. The said fraction 5 is divided into two streams, a first main stream 7 sent to a heat exchanger 8 and then introduced via a pipe 9 into the liquid phase, and a second stream 6 corresponding to the effluent sent to a subsequent stage. The pipe 10 in the bottom of the reaction chamber makes possible the introduction of the catalytic system.

Within the meaning of the present invention, the different embodiments presented can be used alone or in combination with one another, without any limit to the combinations. In the continuation of the description, the subject-matter of the invention is illustrated in the specific case of the oligomerization of gaseous ethylene but also applies to any olefinic feedstocks introduced in the gaseous state into the reactor according to the invention.

It is specified that, throughout this description, the expression "between . . . and . . . " should be understood as including the limits mentioned.

Within the meaning of the present invention, the various ranges of parameters for a given stage, such as the pressure ranges and the temperature ranges, can be used alone or in combination. For example, within the meaning of the present invention, a preferred range of pressure values can be combined with a more preferred range of temperature values.

The invention relates to a gas/liquid reactor for the oligomerization of gaseous ethylene, preferably an upward-flow reactor, which can contain a liquid phase and a gas headspace, the said reactor comprising:
  a chamber 1 of elongated shape along the vertical axis;
  a means for introduction of gaseous ethylene 2, located in the lower part of the reaction chamber;
  a means for withdrawal 5 of a liquid reaction effluent, located in the lower part of the reaction chamber;
  a means for bleeding off 4 a gaseous fraction, located at the top of the said reactor;
in which:
  the said chamber 1 comprises at least two transverse internals 11 positioned over at least a part of a section of the chamber (1) of the said reactor so as to increase the residence time of the gaseous ethylene in the liquid phase;
  each of the said internals exhibiting at least one opening 12 with a hydraulic diameter between 21 and 500 mm; and
  the said opening 12 or the sum of the openings for an internal occupying between 20% and 80% of the total surface area of a cross section of the reaction chamber on which the said internal is located.

The said reactor can also comprise a means for introduction of the gaseous ethylene 2, 3, located in the lower part of the chamber, more particularly in the bottom of the chamber, employing a means for injection of the olefin within the said liquid phase of the reaction chamber. The said reactor can also comprise a means for introduction of the catalytic system 4, located in the lower part, more particularly in the bottom of the reaction chamber.

Preferably, the chamber 1 exhibits a height to width ratio (denoted H/W) between 1 and 8, preferably between 2 and 7. Preferably, the reaction chamber is of cylindrical shape.

The gas/liquid reactor comprises a means for bleeding 4 the gas headspace, located at the top of the reactor.

The gas/liquid reactor comprises a means for withdrawal 5 of a reaction effluent at the bottom of the chamber; preferably, the withdrawal means is located under the means for introduction of the gaseous ethylene.

Preferably, the gas/liquid reactor also comprises a pressure sensor which makes it possible to keep the pressure constant within the reaction chamber. Preferably, the said pressure is kept constant by the introduction of additional olefin into the chamber.

Preferably, the gas/liquid reactor also comprises a liquid level sensor, it being possible for the said level to be kept constant by adjusting the flow rate of the effluent withdrawn in stage c) described below of the process employing the reactor according to the invention.

Preferably, the level sensor is located at the interphase between the liquid phase and the gas headspace.

Transverse Internals

According to the invention, the gas/liquid reactor comprises at least two transverse internals positioned over at least a part of a section of the chamber 1 of the said reactor.

The said transverse internals advantageously make it possible to increase the residence time of the gaseous ethylene, by disrupting the ascent of the gaseous ethylene within the liquid phase, which has the effect of improving the dissolution of the gaseous ethylene and thus of limiting the breakthrough phenomenon.

The transverse internals exhibit at least one opening 12 with a hydraulic diameter between 21 and 500 mm, preferentially between 25 and 450 mm, preferably between 30 and 400 mm.

In a preferred embodiment, the transverse internals 11 exhibit a plurality of openings with a hydraulic diameter between 21 and 500 mm, preferentially between 25 and 450 mm, preferably between 30 and 400 mm.

For each of the internals, the said one opening 12 or the sum of the openings 12 occupy/occupies between 20% and 80% of the total surface area of a cross section of the reaction chamber on which the said internal is located, preferably between 25% and 75%, preferably between 40% and 70%, preferably between 40% and 60% and in a preferred way between 45% and 55%.

In a first embodiment, the said transverse internals 11 extend radially over the entire section of the chamber 1 of the said reactor, so as to be able to slow down the ascent of the gaseous ethylene in the liquid phase when the said reactor is employed.

In this first embodiment, the said transverse internals 11 are preferably chosen from a perforated plate, a slit tray, such as a grid, tray having valves, discs and rings.

In the first embodiment, the said opening 12 corresponds to the perforations, holes, slits or any other gap made in the said internal so as to allow the liquid phase and the gaseous ethylene to pass.

In a second embodiment, the transverse internals 11 extend radially over a part of the section of the chamber 1 of the said reactor, so as to be able to slow down the ascent of the gaseous ethylene in the liquid phase when the said reactor is employed. In other words, in this embodiment, the transverse internals are positioned on the lateral walls of the chamber 1 of the reactor.

Preferably, in this second embodiment, the transverse internals 11 are chosen from flat, curved or pyramidal lateral plates or any other internal capable of acting as baffle.

In the second embodiment, the said opening 12 with a hydraulic diameter between 21 and 500 mm corresponds to the space between one end of the transverse internal and the wall opposite the wall to which the internal is fixed.

In order to reinforce the stability and the sturdiness of the transverse internals with the wall of the chamber of the reactor, integrality is imposed by attaching the transverse internals, for example by welding, by adhesive bonding, by screwing, by bolting or any analogous means. Preferably, the attaching is carried out by welding.

Preferably, the chamber comprises transverse internals 11 according to the first embodiment and the second embodiment.

Figure 4:
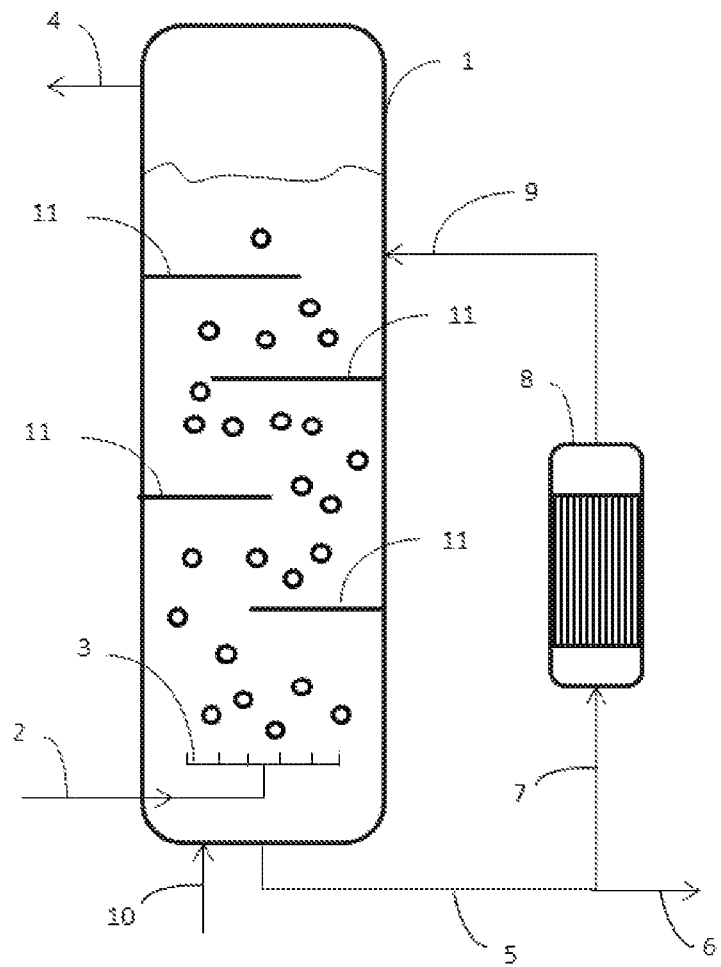
FIG. 4 illustrates a gas/liquid reactor, of bubble column type, according to a second embodiment of the invention, which differs from FIG. 1 in that the chamber comprises four transverse internals of baffle type positioned so as to slow down the ascent of the gaseous ethylene bubbles.
Figure 5:
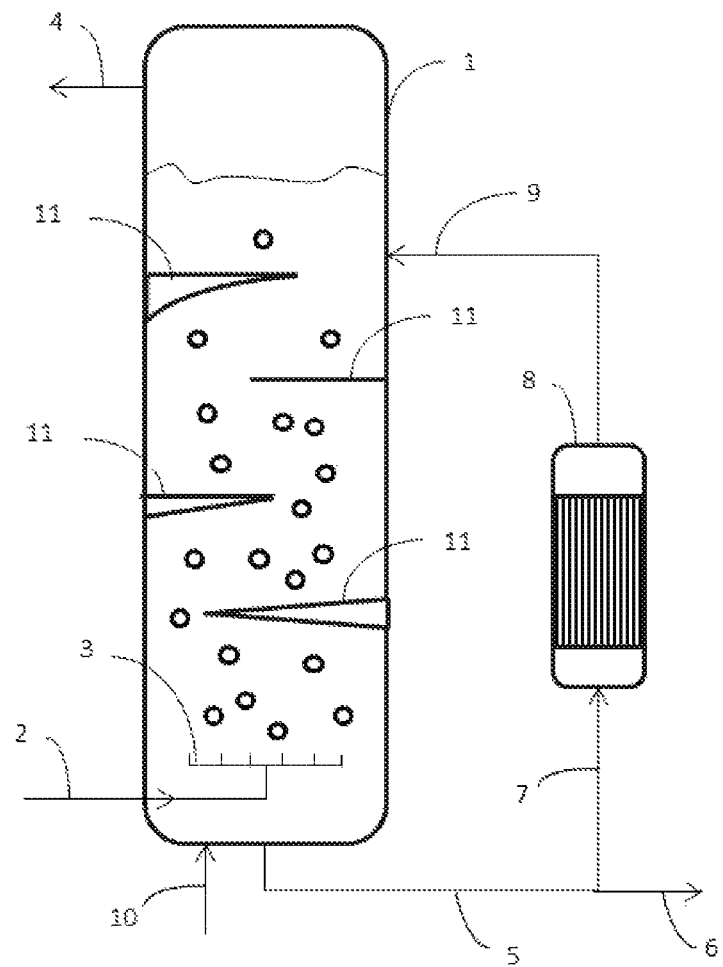
FIG. 5 illustrates a gas/liquid reactor, of bubble column type, according to a third embodiment of the invention, which differs from that of FIG. 4 in that the transverse internals of baffle type have different geometrical shapes.
Figure 6:
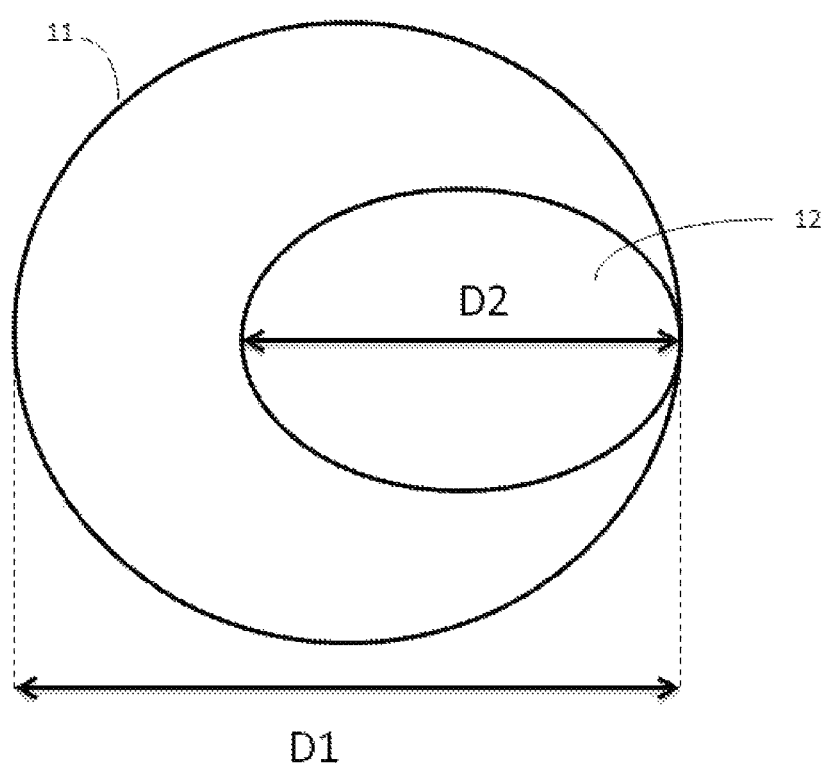
FIG. 6 presents a top view of a transverse internal which can act as baffle, the diameter D1 of which corresponds to the internal diameter of the chamber of the reactor and the diameter D2 of which corresponds to that of the opening.

Preferably, when the chamber comprises several, preferably at least two, transverse internals according to the second embodiment, partially extending over a part of the section of the said chamber, the said internals are positioned alternately on one wall of the chamber and then on the other, as represented diagrammatically in FIGS. 4 and 5.

Preferably, the chamber comprises a number of transverse internals between 2 and 30, preferably between 2 and 20, more preferentially between 2 and 15 and more preferentially still the number of retarders is equal to 2, 3, 4, 5, 6, 7, 8, 9 or 10.

The said transverse internals are capable of allowing the reaction medium, comprising the liquid phase containing gaseous ethylene, to pass and of slowing down the ascent of the said gaseous ethylene within the liquid phase contained in the reaction chamber. In other words, the transverse internals act as retarder and make it possible to increase the residence time of the gaseous ethylene in the liquid phase and thus to increase the dissolution of the ethylene in the said liquid phase. The transverse internals thus make it possible to increase the degree of saturation while limiting the breakthrough phenomenon.

Preferentially, the transverse internals are positioned at equal distance from one another within the reaction chamber.

A Means for Introduction of the Gaseous Ethylene

According to the invention, the reaction chamber comprises a means for introduction of the gaseous ethylene 2 located in the lower part of the said chamber, more particularly in the lateral lower part.

Preferably, the means for introduction of the ethylene is chosen from a pipe, a network of pipes, a multitubular distributor, a perforated plate or any other means known to a person skilled in the art.

In a specific embodiment, the means for introduction of the ethylene is located in the recirculation loop.

Preferably, a gas distributor 3, which is a device which makes it possible to disperse the gaseous ethylene uniformly over the entire liquid section, is positioned at the end of the introduction means within the reaction chamber. The said device comprises a network of perforated pipes, the diameter of the orifices of which is between 1.0 and 12.0 mm, preferably between 3.0 and 10.0 mm, in order to form ethylene bubbles of millimetric size in the liquid.

An Optional Means for Introduction of the Catalytic System

Advantageously, the chamber comprises a means for introduction of the catalytic system 10.

Preferably, the introduction means is located on the lower part of the chamber and preferably at the bottom of the said chamber.

According to an alternative embodiment, the catalytic system is introduced into the recirculation loop.

The means for introduction of the catalytic system is chosen from any means known to a person skilled in the art and is preferably a pipe.

In the embodiment where the catalytic system is employed in the presence of a solvent or of a mixture of solvents, the said solvent is introduced by an introduction means located in the lower part of the chamber, preferably at the bottom of the chamber, or else into the recirculation loop.

An Optional Recirculation Loop

Advantageously, the liquid phase can be rendered homogeneous and also the temperature can be regulated within the chamber of the reactor according to the invention by the use of a recirculation loop comprising a means on the lower part of the chamber, preferably at the bottom, in order to withdraw a liquid fraction to one or more heat exchanger(s) making possible the cooling of the said liquid, and a means for introduction of the said cooled liquid into the liquid phase in the upper part of the chamber.

The recirculation loop makes possible good homogenization of the concentrations and also makes possible control of the temperature in the liquid phase within the chamber.

Advantageously, the use of a recirculation loop makes it possible to induce a direction of circulation of the liquid phase in the chamber from the upper part to the lower part of the said chamber, which makes it possible to increase the residence time of the gaseous ethylene by slowing down its rise in the said liquid phase and thus to further limit the breakthrough phenomenon.

The recirculation loop can advantageously be implemented by any necessary means known to a person skilled in the art, such as a pump for the withdrawal of the liquid fraction, a means capable of regulating the flow rate of the withdrawn liquid fraction, or else a pipe for bleeding off at least a portion of the liquid fraction.

Preferably, the means for withdrawal of the liquid fraction from the chamber is a pipe.

The heat exchanger(s) capable of cooling the liquid fraction is (are) chosen from any means known to a person skilled in the art.

An Optional Loop for Recycling the Gas Headspace

Advantageously, the gas/liquid oligomerization reactor according to the invention additionally comprises a loop for recycling the gas headspace into the lower part of the liquid phase. The said loop comprises a means for withdrawal of a gaseous fraction at the gas headspace located in the upper part of the chamber and a means for introduction of the said withdrawn gaseous fraction into the liquid phase in the lower part of the said chamber.

The recycle loop advantageously makes it possible to compensate for the breakthrough phenomenon and to limit the loss in productivity of the reactor, while keeping the saturation in dissolved ethylene in the liquid phase close to the desired value.

Another advantage of the recycle loop is to improve the volume productivity of the device and thus to reduce the costs. In a preferred embodiment, the recycle loop additionally comprises a compressor.

In one embodiment, the withdrawn gaseous fraction is introduced via the means for introduction of the gaseous ethylene.

In another embodiment, the withdrawn gaseous fraction is introduced via a gas distributor which is a device which makes it possible to disperse the gaseous fraction uniformly over the entire liquid section and is positioned at the end of the introduction means within the chamber. The said device comprises a network of perforated pipes, the diameter of the orifices of which is between 1.0 and 12.0 mm, preferably between 3.0 and 10.0 mm, in order to form ethylene bubbles of millimetric size in the liquid.

Preferably, the means for introduction of the withdrawn gaseous fraction is chosen from a pipe, a network of pipes, a multitubular distributor, a perforated plate or any other means known to a person skilled in the art.

Oligomerization Process

Another subject-matter of the present invention covers an oligomerization process employing the gas/liquid reactor according to the invention as described above.

Preferably, in a gas/liquid reactor, the flow rate of gaseous ethylene introduced in stage b), as described below, is controlled by the pressure in the reaction chamber. Thus, in the case of an increase in the pressure in the reactor as a result of a high level of breakthrough of the ethylene into the gas headspace, the flow rate of gaseous ethylene introduced in stage b), as described below, decreases, which leads to a decrease in the amount of ethylene dissolved in the liquid phase, and thus in the ethylene saturation. The said decrease is detrimental to the conversion of the ethylene and is accompanied by a decrease in the productivity of the reactor, and possibly in its selectivity.

Advantageously, the use of the reactor according to the invention in an oligomerization process, preferably oligomerization by homogeneous catalysis, makes it possible to have a degree of saturation in dissolved ethylene in the liquid phase of greater than 70.0%, preferably between 70.0% and 100%, preferably between 80.0% and 100%, in a preferred way between 80.0% and 99.0%, preferably between 85.0% and 99.0% and more preferably still between 89.0% and 98.0%.

The degree of saturation in dissolved ethylene can be measured by any method known to a person skilled in the art and, for example, by gas chromatography (commonly referred to as GC) analysis of a fraction of the liquid phase withdrawn from the reaction chamber.

The process employing the gas/liquid reactor according to the invention makes it possible to obtain linear olefins and in particular linear α-olefins by bringing olefin(s), in particular ethylene, and a catalytic system into contact, optionally in the presence of an additive and/or of a solvent, and by the use of the said gas/liquid reactor according to the invention.

All catalytic systems known to a person skilled in the art and capable of being employed in the dimerization, trimerization or tetramerization processes and more generally in the oligomerization processes according to the invention come within the field of the invention. The said catalytic systems and also their uses are described in particular in Applications FR 2 984 311, FR 2 552 079, FR 3 019 064, FR 3 023 183, FR 3 042 989 or else in Application FR 3 045 414.

Preferably, the catalytic systems comprise, preferably consist of:
 a metal precursor, preferably based on nickel, on titanium or on chromium,
 an activating agent,
 optionally an additive, and
 optionally a solvent.

The Metal Precursor

The metal precursor used in the catalytic system is chosen from compounds based on nickel, on titanium or on chromium.

In one embodiment, the metal precursor is based on nickel and preferentially comprises nickel of (+II) oxidation state. Preferably, the nickel precursor is chosen from nickel(II) carboxylates, such as, for example, nickel 2-ethylhexanoate, nickel(II) phenates, nickel(II) naphthenates, nickel(II) acetate, nickel(II) trifluoroacetate, nickel(II) triflate, nickel (II) acetylacetonate, nickel(II) hexafluoroacetylacetonate, π-allylnickel(II) chloride, π-allylnickel(II) bromide, methallylnickel(II) chloride dimer, η³-allylnickel(II) hexafluorophosphate, η³-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferentially comprises a titanium aryloxy or alkoxy compound.

The titanium alkoxy compound advantageously corresponds to the general formula [Ti(OR)$_4$] in which R is a linear or branched alkyl radical. Mention may be made, among the preferred alkoxy radicals, as non-limiting examples, of tetraethoxy, tetraisopropoxy, tetra(n-butoxy) and tetra(2-ethylhexyloxy).

The titanium aryloxy compound advantageously corresponds to the general formula [Ti(OR')$_4$] in which R' is an aryl radical substituted or unsubstituted by alkyl or aryl groups. The radical R' can comprise heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl) phenoxy, 4-methyl-2,6-di(tert-butyl)phenoxy, 2,6-dichloro-4-(tert-butyl)phenoxy and 2,6-dibromo-4-(tert-butyl) phenoxy, the biphenoxy radical, binaphthoxy or 1,8-naphthalenedioxy.

According to a third embodiment, the metal precursor is based on chromium and preferentially comprises a chromium(II) salt, a chromium(III) salt or a salt of different oxidation state which can comprise one or more identical or different anions, such as, for example, halides, carboxylates, acetylacetonates or alkoxy or aryloxy anions. Preferably, the chromium-based precursor is chosen from CrCl$_3$, CrCl$_3$ (tetrahydrofuran)$_3$, Cr(acetylacetonate)$_3$, Cr(naphthenate)$_3$, Cr(2-ethylhexanoate)$_3$ and Cr(acetate)$_3$.

The concentration of nickel, of titanium or of chromium is between 0.01 and 300.0 ppm by weight of atomic metal, with respect to the reaction mass, preferably between 0.02 and 100.0 ppm, preferentially between 0.03 and 50.0 ppm, more preferentially between 0.5 and 20.0 ppm and more preferentially still between 2.0 and 50.0 ppm by weight of atomic metal, with respect to the reaction mass.

The Activating Agent

Whatever the metal precursor, the catalytic system additionally comprises one or more activating agents chosen from aluminium-based compounds, such as methylaluminium dichloride (MeAlCl$_2$), dichloroethylaluminum (EtAlCl$_2$), ethylaluminium sesquichloride (Et$_3$Al$_2$Cl$_3$), chlorodiethylaluminum (Et$_2$AlCl), chlorodiisobutylaluminium (i-Bu$_2$AlCl), triethylaluminium (AlEt$_3$), tripropylaluminium (Al(n-Pr)$_3$), triisobutylaluminium (Al(i-Bu)$_3$), diethylethoxyaluminium (Et$_2$AlOEt), methylaluminoxane (MAO), ethylaluminoxane and modified methylaluminoxanes (MMAO).

The Additive

Optionally, the catalytic system comprises one or more additives.

When the catalytic system is based on nickel, the additive is chosen from:
compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2, 3-diimine, N,N'-bis(2,6-dimethylphenyl)butane-2,3-diimine or N,N'-bis(2,6-diisopropylphenyl)butane-2,3-diimine, or compounds of phosphine type independently chosen from tributylphosphine, triisopropylphosphine, tricyclopentylphosphine, tricyclohexylphosphine, triphenylphosphine, tris(o-tolyl)phosphine, bis(diphenylphosphino) ethane, trioctylphosphine oxide, triphenylphosphine oxide or triphenyl phosphite, or compounds corresponding to the general formula (I) or one of the tautomers of the said compound:

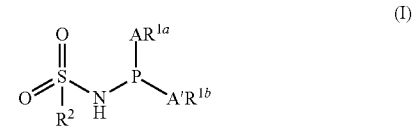

(I)

in which:
A and A', which are identical or different, are independently an oxygen or a single bond between the phosphorus atom and a carbon atom,
the R$^{1a}$ and R$^{1b}$ groups are independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-di(trifluoromethyl)phenyl, benzyl, naphthyl, bisnaphthyl, pyridyl, bisphenyl, furanyl or thiophenyl groups,
the R$^2$ group is independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl or thiophenyl groups.

When the catalytic system is based on titanium, the additive is chosen from diethyl ether, diisopropyl ether, dibutyl ether, diphenyl ether, 2-methoxy-2-methylpropane, 2-methoxy methylbutane, 2,2-dimethoxypropane, 2,2-bis(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, bis(2-methoxyethyl) ether, benzofuran, glyme and diglyme, taken alone or as a mixture.

When the catalytic system is based on chromium, the additive is chosen from:
- compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, and/or
- aryloxy compounds of general formula $[M(R^3O)_{2-n}X_n]_y$, in which:
  M is chosen from magnesium, calcium, strontium and barium, preferably magnesium,
  $R^3$ is an aryl radical containing from 6 to 30 carbon atoms and X is a halogen or an alkyl radical containing from 1 to 20 carbon atoms,
  n is an integer which can take the values of 0 or 1, and
  y is an integer between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals can be carried by one and the same molecule, such as, for example, the biphenoxy radical, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy.

The Solvent

In another embodiment according to the invention, the catalytic system optionally comprises one or more solvents.

The solvent is chosen from the group formed by aliphatic and cycloaliphatic hydrocarbons, such as hexane, cyclohexane, heptane, butane or isobutane.

Preferably, the solvent used is cyclohexane.

In one embodiment, a solvent or a mixture of solvents can be used during the oligomerization reaction. The said solvent is advantageously chosen independently from the group formed by aliphatic and cycloaliphatic hydrocarbons, such as hexane, cyclohexane, heptane, butane or isobutane.

Preferably, the linear α-olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear α-olefins chosen from but-1-ene, hex-1-ene or oct-1-ene.

Advantageously, the oligomerization process is carried out at a pressure between 0.1 and 10.0 MPa, preferably between 0.2 and 9.0 MPa and preferentially between 0.3 and 8.0 MPa, at a temperature between 30 and 200° C., preferably between 35 and 150° C. and in a preferred way between 45 and 140° C.

Preferably, the concentration of catalyst is between 0.01 and 500.0 ppm by weight of atomic metal, with respect to the reaction mass, preferably between 0.05 and 100.0 ppm, preferably between 0.1 and 50.0 ppm and preferably between 0.2 and 30.0 ppm by weight of atomic metal, with respect to the reaction mass.

According to another embodiment, the oligomerization process is carried out continuously. The catalytic system, constituted as described above, is injected at the same time as the ethylene into a reactor stirred by conventional mechanical means known to a person skilled in the art or by external recirculation, and maintained at the desired temperature. The components of the catalytic system can also be injected separately into the reaction medium. The gaseous ethylene is introduced by an inlet valve controlled by the pressure, which keeps the latter constant in the reactor. The reaction mixture is withdrawn by means of a valve controlled by the liquid level, so as to keep the latter constant. The catalyst is destroyed continuously by any usual means known to a person skilled in the art and then the products resulting from the reaction, and also the solvent, are separated, for example by distillation. The ethylene which has not been converted can be recycled into the reactor. The catalyst residues included in a heavy fraction can be incinerated.

Stage a) of Introduction of the Catalytic System

The process employing the gas/liquid reactor according to the invention comprises a stage a) of introduction of a catalytic system comprising a metal catalyst and an activating agent, and optionally of a solvent or of a mixture of solvents, into a reaction chamber comprising a liquid phase in a lower part and a gas headspace in an upper part.

Preferably, the catalytic system is introduced into the liquid phase in the lower part of the reaction chamber and preferably in the bottom of the reaction chamber.

Preferably, the pressure for introduction into the reaction chamber is between 0.1 and 10.0 MPa, preferably between 0.2 and 9.0 MPa and preferentially between 0.3 and 8.0 MPa.

Preferably, the temperature for introduction into the reaction chamber is between 30 and 200° C., preferably between 35 and 150° C. and in a preferred way between 45 and 140° C.

Stage b) of Bringing into Contact with Gaseous Ethylene

The process employing the gas/liquid reactor according to the invention comprises a stage b) of bringing the catalytic system introduced in stage a) into contact with gaseous ethylene. The said gaseous ethylene is introduced into the liquid phase at the lower part of the reaction chamber, preferably on the lateral lower part of the reaction chamber. The gaseous ethylene introduced comprises fresh gaseous ethylene, and preferably the said fresh gaseous ethylene is combined with gaseous ethylene recycled from a separation stage subsequent to the oligomerization process.

During the implementation of the process according to the invention, following the stage of introduction of the gaseous ethylene, the liquid phase comprises undissolved gaseous ethylene; thus, according to the zones of the reaction chamber, the liquid phase corresponds to a gas/liquid mixture between in particular the liquid phase and the gaseous ethylene. Preferably, the zone in the bottom of the reaction chamber below the level at which the gaseous ethylene is introduced comprises, preferably is constituted of, the liquid phase without gaseous ethylene.

Preferably, the gaseous ethylene is distributed by dispersion during its introduction into the lower liquid phase of the reaction chamber by a means capable of carrying out the said dispersion uniformly over the entire section of the reactor. Preferably, the dispersion means is chosen from a distributor network with a homogeneous distribution of the ethylene injection points over the entire section of the reactor.

Preferably, the velocity of the gaseous ethylene at the outlet of the orifices is between 1.0 and 30.0 m/s. Its superficial velocity (volumetric gas velocity divided by the section of the reaction chamber) is between 0.5 and 10.0 cm/s and preferably between 1.0 and 8.0 cm/s.

Preferably, the gaseous ethylene is introduced at a flow rate between 1 and 250 t/h, preferably between 3 and 200 t/h, preferably between 5 and 150 t/h and preferably between 10 and 100 t/h.

Preferably, the flow rate of gaseous ethylene introduced in stage b) is controlled by the pressure in the reaction chamber.

According to a specific implementation of the invention, a stream of gaseous hydrogen can also be introduced into the reaction chamber, with a flow rate representing from 0.2% to 1.0% by weight of the flow rate of incoming ethylene. Preferably, the stream of gaseous hydrogen is introduced by the pipe employed for the introduction of the gaseous ethylene.

Stage c) of Withdrawal of a Fraction of the Liquid Phase

The process employing the gas/liquid reactor according to the invention comprises a stage c) of withdrawal of a fraction of the liquid phase, preferably in the lower part of the reaction chamber.

The withdrawal implemented in stage c) is preferably carried out in the lower part of the reaction chamber, preferably below the level of injection of gaseous ethylene, and preferably in the bottom of the chamber. The withdrawal is carried out by any means capable of carrying out the withdrawal and preferably by a pump.

Preferably, the withdrawal flow rate is between 500 and 10 000 t/h and preferably between 800 and 7000 t/h.

In one embodiment, a second stream is withdrawn from the liquid phase. The said second stream corresponds to the effluent obtained on conclusion of the oligomerization process and can be sent to a separation section located downstream of the device employed in the process according to the invention.

According to a preferred embodiment, the liquid fraction withdrawn from the liquid phase is divided into two streams. The first "main" stream is sent to the cooling stage d) and the second stream corresponds to the effluent and is sent to the downstream separation section.

Advantageously, the flow rate of the said second stream is regulated so as to maintain a constant liquid level in the reactor. Preferably, the flow rate of the said second stream is from 5 to 200 times lower than that of the liquid stream sent to the cooling stage. Preferably, the flow rate of the said effluent is from 5 to 150 times lower, preferably from 10 to 120 times lower and preferably from 20 to 100 times lower.

Stage d) of Cooling the Liquid Fraction

The process employing the gas/liquid reactor according to the invention comprises a stage d) of cooling the liquid fraction withdrawn in stage c).

Preferably, the cooling stage is carried out by the circulation of the main liquid stream withdrawn in stage c) through one or more heat exchangers located inside or outside the reaction chamber and preferably outside.

The heat exchanger makes it possible to reduce the temperature of the liquid fraction by 1.0 to 30.0° C., preferably between 2.0 and 20° C., preferably between 2.0 and 15.0° C., preferably between 2.5 and 10.0° C., preferably by 3.0 to 9.0° C., preferably by 4.0 to 8.0° C. Advantageously, the cooling of the liquid fraction makes it possible to keep the temperature of the reaction medium within the desired temperature ranges.

Advantageously, the implementation of the stage of cooling the liquid via the recirculation loop also makes it possible to carry out the stirring of the reaction medium and thus to homogenize the concentrations of the reactive entities throughout the liquid volume of the reaction chamber.

Stage e) of Introduction of the Cooled Liquid Fraction

The process employing the gas/liquid reactor according to the invention comprises a stage e) of introduction of the liquid fraction cooled in stage d).

The introduction of the cooled liquid fraction resulting from stage d) is carried out in the liquid phase of the reaction chamber, preferably in the upper part of the said chamber, by any means known to a person skilled in the art.

Advantageously, when the cooled fraction is introduced into the upper part of the liquid phase contained in the reaction chamber, a direction of circulation of the said liquid phase is induced from the top to the bottom of the said chamber, which slows down the rise of the gaseous ethylene in the liquid phase and thus improves the dissolution of the ethylene in the liquid phase. Thus, the combination of this embodiment and of the reactor comprising transverse internals according to the invention makes it possible to even better limit the breakthrough phenomenon.

Preferably, the flow rate for introduction of the cooled liquid fraction is between 500 and 10 000 t/h and preferably between 800 and 7000 t/h.

Stages c) to e) constitute a recirculation loop. Advantageously, the recirculation loop makes it possible to carry out the stirring of the reaction medium and thus to homogenize the concentrations of the reactive entities throughout the liquid volume of the reaction chamber.

Optional Stage f) of Recycling a Gaseous Fraction Withdrawn from the Gas Headspace Advantageously, the process employing the gas/liquid reactor according to the invention comprises a stage f) of recycling a gaseous fraction withdrawn from the gas headspace of the reaction chamber and introduced at the lower part of the reaction chamber into the liquid phase, preferably on the lateral lower part of the reaction chamber, preferably at the bottom of the reaction chamber.

The optional stage f) of recycling the gaseous fraction is also known as recycle loop. The withdrawal of the gaseous fraction implemented in stage f) is carried out by any means capable of carrying out the withdrawal and preferably by a compressor.

An advantage of the optional recycling stage f) is that of making it possible to compensate in a simple and economic way for the phenomenon of breakthrough of the gaseous ethylene into the gas headspace in an oligomerization process, whatever the dimensions of the reactor according to the invention.

The breakthrough phenomenon corresponds to the gaseous ethylene which crosses the liquid phase without dissolving and which passes into the gas headspace. When the flow rate of injected gaseous ethylene and the headspace volume are fixed at a given value, the breakthrough then leads to an increase in pressure in the reaction chamber. In a gas/liquid reactor employed according to a preferred process, the flow rate for introduction of the ethylene in stage b) is controlled by the pressure in the reaction chamber. Thus, in the case of an increase in the pressure in the reactor as a result of a high level of breakthrough of the ethylene into the gas headspace, the flow rate of gaseous ethylene introduced in stage b) decreases, which leads to a decrease in the amount of ethylene dissolved in the liquid phase and thus in the saturation. The decrease in the saturation is detrimental to the conversion of the ethylene and is accompanied by a decrease in the productivity of the reactor. The optional stage of recycling a gaseous fraction advantageously makes it possible to optimize the saturation of the dissolved ethylene and thus to improve the volume productivity of the process.

The gaseous fraction withdrawn in stage f) can be introduced into the reaction chamber alone or as a mixture with the gaseous ethylene introduced in stage b). Preferably, the gaseous fraction is introduced as a mixture with the gaseous ethylene introduced in stage b).

In a specific embodiment, the gaseous fraction withdrawn in stage f) is introduced into the reaction chamber by dispersion in the lower liquid phase of the reaction chamber by a means capable of carrying out the said dispersion uniformly over the entire section of the reactor. Preferably, the dispersion means is chosen from a distributor network with a homogeneous distribution of the points for injection of the gaseous fraction withdrawn in stage f) over the entire section of the reactor.

Preferably, the velocity of the withdrawn gaseous fraction at the outlet of the orifices is between 1.0 and 30.0 m/s. Its superficial velocity (volumetric gas velocity divided by the section of the reaction chamber) is between 0.5 and 10.0 cm/s and preferably between 1.0 and 8.0 cm/s.

Preferably, the flow rate for withdrawal of the fraction is between 0.1% and 100% of the flow rate of gaseous ethylene introduced in stage b), preferably 0.5% and 90.0%, preferably 1.0% and 80.0%, preferably between 2.0% and 70.0%, preferably between 4.0% and 60.0%, preferably between 5.0% and 50.0%, preferably between 10.0% and 40.0% and in a preferred way between 15.0% and 30.0%.

Advantageously, the flow rate for withdrawal of the gaseous fraction in stage f) is controlled by the pressure within the reaction chamber, which makes it possible to maintain the pressure at a desired value or in a desired range of values and thus to compensate for the phenomenon of breakthrough of the gaseous ethylene into the headspace.

In a specific embodiment, the gaseous fraction withdrawn in stage f) is divided into two streams: a first "main" gas stream, which is recycled directly into the reaction chamber, and a second gas stream.

In a preferred embodiment, the said second gas stream corresponds to a bleeding of the gas headspace, which makes it possible to remove a part of the non-condensable gases.

Preferably, the flow rate of the second gas stream is between 0.005% and 1.00% of the flow rate of ethylene introduced in stage b), preferably between 0.01% and 0.50%.

EXAMPLES

The examples below illustrate the invention without limiting the scope thereof.

Example 1 (Comparative)

Example 1 illustrates the reference case corresponding to FIG. 1, in which the oligomerization process employs a gas/liquid reactor according to the prior art.

A gas/liquid oligomerization reactor according to the prior art, comprising a reaction chamber of cylindrical shape having a diameter of 1.8 m and a liquid height of 6 m, is employed at a pressure of 7.0 MPa and at a temperature of 120° C.

The catalytic system introduced into the reaction chamber is a chromium-based catalytic system, as described in Patent FR 3 019 064, in the presence of cyclohexane as solvent.

The said catalytic system is brought into contact with ethylene by introduction of the said gaseous ethylene into the lower part of the said chamber. The effluent is subsequently recovered at the reactor bottom.

The volume productivity of this reactor is 17 kg of α-olefin produced per hour and per $m^3$ of reaction volume.

The performance qualities of this reactor make it possible to convert 77.4% of the injected ethylene, for a degree of saturation in dissolved ethylene in the liquid phase of 61.0%, and to achieve a selectivity of 83.1% for hex-1-ene, for a degree by weight of solvent of 1.6. The said degree of solvent is calculated as the ratio by weight of the flow rate of injected solvent to the flow rate of injected gaseous ethylene.

Figure 2:
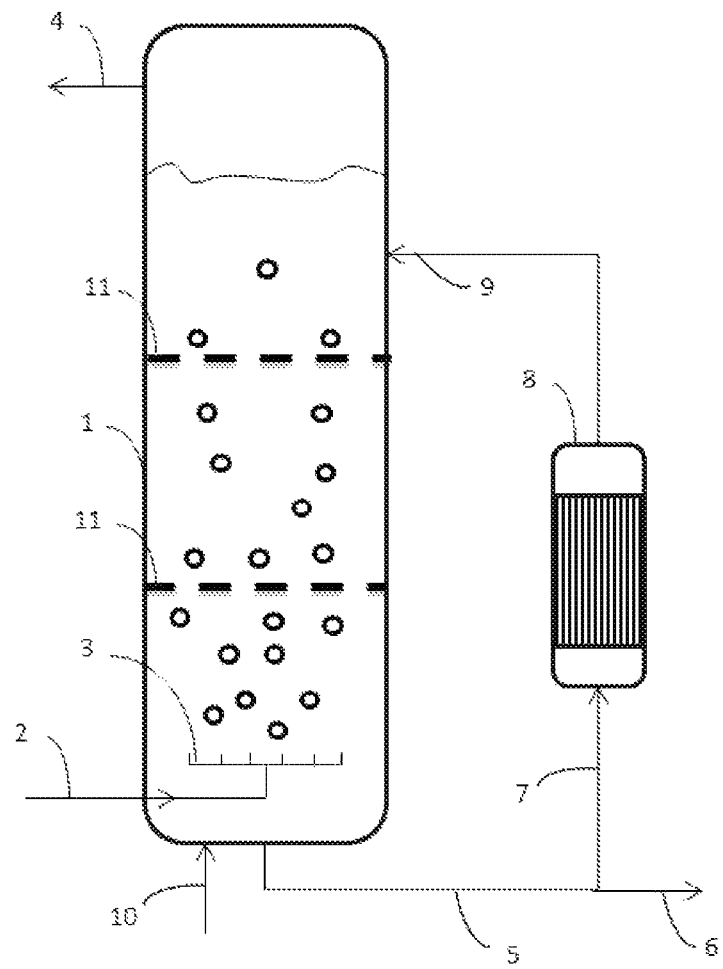
FIG. 2 illustrates a gas/liquid reactor, of bubble column type, according to a first embodiment of the invention, which differs from FIG. 1 in that the reaction chamber comprises two transverse internals of perforated tray type so as to slow down the ascent of the gaseous ethylene bubbles.
Figure 3:
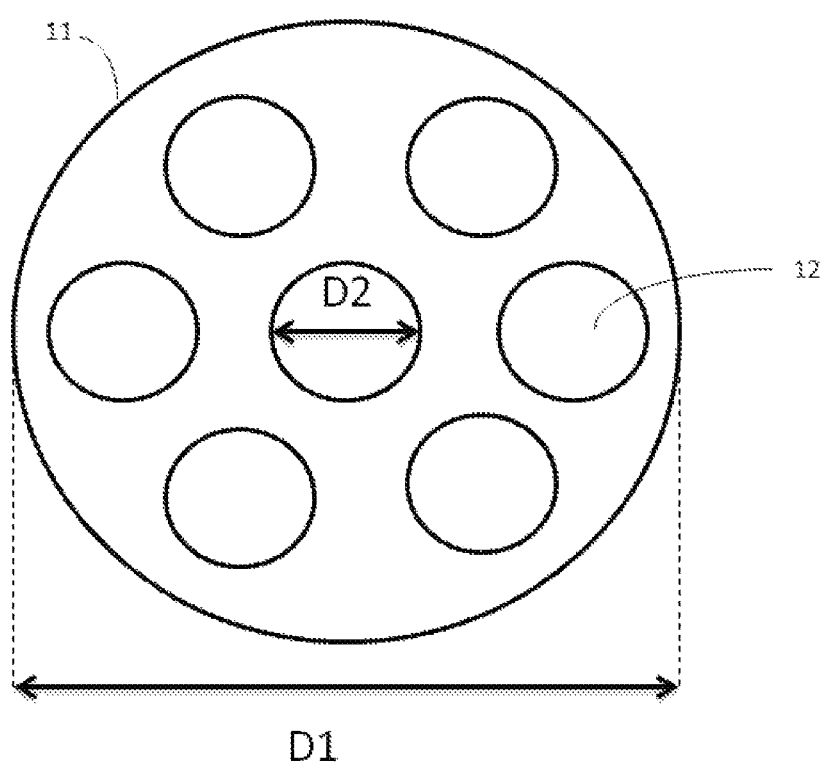
FIG. 3 presents a top view of a transverse internal 11 of the reactor according to FIG. 2; the said internal is a tray, each perforation 12 of which exhibits a hydraulic diameter D2 and the diameter D1 of which corresponds to the internal diameter of the reaction chamber.

Example 2: According to the Invention Corresponding to FIG. 2

A reactor according to the invention having two perforated plates as transverse internals is employed under the same conditions as Example 1.

Each of the perforated plates has the following characteristics:

plurality of openings 12 with a hydraulic diameter of 0.44 metre, the sum of the openings 12 occupying 30% of the total surface area of a cross section of the chamber for each of the perforated plates 11.

The volume productivity of this reactor is 38.3 kg of α-olefin produced per hour and per $m^3$ of reaction volume.

The performance qualities of this reactor make it possible to convert 57.8% of the injected ethylene, for a degree of saturation in dissolved ethylene in the liquid phase of 89.0%, and to achieve a selectivity of 87.5% for the desired α-olefin, for a degree by weight of solvent of 1.6. The said degree of solvent is calculated as the ratio by weight of the flow rate of injected solvent to the flow rate of injected gaseous ethylene.

In this example, the reactor according to the invention makes it possible to increase the saturation of the ethylene by 28%, to increase the selectivity for α-olefin by 4.3% and to multiply the productivity by 2.25, in comparison with the case according to the prior art of Example 1.

The invention claimed is:
1. A process for the oligomerization of gaseous ethylene employing a reactor comprising:
   a reaction chamber (1) of elongated shape along the vertical axis;
   a means for introduction of gaseous ethylene (2), located in a lower part of the reaction chamber;
   a means for withdrawal (5) of a liquid fraction, located in the lower part of the reaction chamber;
   a means for introducing a portion of the liquid fraction into a heat exchanger which is in fluid communication with said means for withdrawal (5) of the liquid fraction, and a means for removing said portion of the liquid fraction from said heat exchanger and introducing said portion of the liquid fraction into a top part of the reaction chamber (1), a means for bleeding off (4) a gaseous fraction, located at a top part of said reaction chamber;

wherein:

said chamber (1) comprises two or more transverse internals (11) wherein each transverse internal (11) is positioned over at least a part of a cross section of the reaction chamber (1) so as to increase residence time of gaseous ethylene in a liquid phase;

each of said internals exhibiting one or more openings (12) with a hydraulic diameter between 21 and 500 mm; and said one or more openings (12) occupying between 20% and 80% of the total surface area of the cross section of the reaction chamber at which said internal is located, and wherein said process comprises:

introducing a metal catalyst and an activating agent into the reaction chamber, bringing said metal catalyst and the activating agent into contact with gaseous ethylene by the introduction of said gaseous ethylene into the lower part of the reaction chamber, withdrawing the liquid fraction, cooling the withdrawn liquid fraction by passing said liquid fraction through the heat exchanger, introducing the cooled withdrawn liquid fraction into a top part of the reaction chamber, recycling the gaseous fraction, withdrawn at a gas headspace positioned at an upper part of the top part of the reaction chamber by the means for bleeding off, and introducing the gaseous fraction at the lower part of the reaction chamber, into the liquid phase, and wherein said process is carried out at a pressure between 0.1 and 10.0 MPa and at a temperature between 30 and 200° C.

2. The process of claim 1, in which the transverse internals exhibit at least one opening (12) with a hydraulic diameter between 25 and 450 mm.

3. The process of claim 1, in which the transverse internals (11) exhibit a plurality of openings with a hydraulic diameter between 21 and 500 mm.

4. The process of claim 1, wherein said one or more openings (12) occupy/occupies between 25% and 75% of the total surface area of the cross section of the chamber on which said internal is located.

5. The process of claim 1, in which the transverse internals (11) extend radially across a width of the chamber (1) of said reactor, and are suitable to slow down the ascent of the gaseous ethylene in the liquid phase.

6. The process of claim 1, in which the transverse internals (11) are chosen from a perforated plate, a slit tray, a tray having valves, discs, and rings.

7. The process of claim 1, in which the transverse internals (11) extend radially across only a portion of a width of the chamber (1) of said reactor, so as to be able to slow down the ascent of the gaseous ethylene in the liquid phase.

8. The process of claim 1, in which the transverse internals (11) are selected from the group consisting of flat, curved, and pyramidal lateral plates.

9. The process of claim 1, comprising at least two transverse internals (11), wherein the at least two transverse internals (11) are positioned alternately on the walls of the chamber (1).

10. The process of claim 1, in which the chamber comprises a number of transverse internals between 2 and 30.

11. The process of claim 1, wherein the transverse internals exhibit at least one opening (12) with a hydraulic diameter between 30 and 400 mm.

12. The process of claim 1, wherein the transverse internals (11) exhibit a plurality of openings with a hydraulic diameter between 25 and 450 mm.

13. The process of claim 1, wherein the transverse internals (11) exhibit a plurality of openings with a hydraulic diameter between 30 and 400 mm.

14. The process of claim 1, wherein said one or more openings (12) occupy/occupies between 40% and 70% of the total surface area of the cross section of the chamber on which the said internal is located.

15. The process of claim 1, wherein the chamber comprises a number of transverse internals between 2 and 20.

16. The process of claim 1, wherein the chamber comprises a number of transverse internals between 2 and 15.

* * * * *